(12) United States Patent
Kessler et al.

(10) Patent No.: US 8,303,994 B2
(45) Date of Patent: Nov. 6, 2012

(54) **METHOD FOR THE ERADICATION OF PATHOGENS INCLUDING *S. AUREUS* AND ANTIBIOTIC RESISTANT MICROBES FROM THE UPPER RESPIRATORY TRACT OF MAMMALS AND FOR INHIBITING THE ACTIVATION OF IMMUNE CELLS**

(76) Inventors: Jack Howard Kessler, Southborough, MA (US); James Carlton Richards, Sudbury, MA (US)

( * ) Notice: Subject to any disclaimer, the term of this patent is extended or adjusted under 35 U.S.C. 154(b) by 1149 days.

(21) Appl. No.: 11/473,759

(22) Filed: Jun. 22, 2006

(65) Prior Publication Data

US 2007/0298126 A1    Dec. 27, 2007

(51) Int. Cl.
*A01N 59/00* (2006.01)
*A01N 59/08* (2006.01)
*A01N 59/10* (2006.01)
*A01N 59/22* (2006.01)

(52) U.S. Cl. .......... 424/667; 424/51; 424/668; 424/669; 424/670; 424/671

(58) Field of Classification Search ........................ None
See application file for complete search history.

(56) References Cited

U.S. PATENT DOCUMENTS

| | | | |
|---|---|---|---|
| 2,739,922 A | | 3/1956 | Shelanski |
| 5,885,592 A | | 3/1999 | Duan et al. |
| 5,962,029 A | | 10/1999 | Duan et al. |
| 6,004,587 A | * | 12/1999 | Mullerat et al. ............. 424/661 |
| 6,063,363 A | * | 5/2000 | Goodwin et al. ............. 424/45 |
| 6,099,855 A | * | 8/2000 | Mullerat et al. ............. 424/442 |
| 6,171,611 B1 | | 1/2001 | Picciano |
| 6,663,902 B1 | * | 12/2003 | Hei et al. ............. 424/661 |

OTHER PUBLICATIONS

Philippe Corne, et al., Molecular evidence that nasal carriage of *Staphylococcus aureus* plays a role in respiratory tract infections of critically ill patients; J Clin Microbiol 2005, 43, 3491-3493.
Waldemar Gottardi, Iodine and Disinfection: Theoretical Study on Mode of Action, Efficiency, Stability, and Analytical Aspects in the Aqueous System; Arch. Pharm. Med. Chem. 1999, 332, 151-157.
Waldemar Gottardi, Potentiometric Evaluation of the Equilibrium Concentrations of Free and Complex Bound Iodine in Aqueous Solutions of Polyvinylpyrrolidone-Iodine (Povidone-Iodine); Fresenius Z. Anal. Chem. 1983, 314, 582-585.
K. Reimer, et al., Antimicrobial Effectiveness of Povidone-Iodine and Consequences for New Application Areas; Dermatology 2002, 2004, Suppl. 1, 114-120.
Miranda M.L. Van Rijen, et al., Intranasal mupirocin for reduction of *Staphylococcus aureus* infections in surgical patients with nasal carriage: a systematic review; Journal of Antimicrobial Chemotherapy 2008, 61, 254-261.
W. Gottardi, Iodine and Iodine Compounds; Disinfectants and Antiseptics, A. By Chemical Type, Chapter 8, 152-165, 1991.
Jack Kessler, Ph.D., et al., Factors Influencing the Study of Peroxidase-Generated Iodine Species and Implications for Thyroglobulin Synthesis, Thyroid, vol. 18, No. 7, 2008, 769-774.

* cited by examiner

*Primary Examiner* — Debbie K Ware

(57) ABSTRACT

A method for killing or substantially eradicating a pathogen in the upper respiratory tract of a mammal is disclosed. The method comprises generating molecular iodine (I2) in situ using an oxidant-reductant reaction with a minimum concentration of at least about 25 ppm of I2 and I2 comprises at least 40% of the total iodine atoms. A method for inhibiting superantigens using molecular iodine is also disclosed.

9 Claims, No Drawings

METHOD FOR THE ERADICATION OF PATHOGENS INCLUDING S. AUREUS AND ANTIBIOTIC RESISTANT MICROBES FROM THE UPPER RESPIRATORY TRACT OF MAMMALS AND FOR INHIBITING THE ACTIVATION OF IMMUNE CELLS

FIELD

The application of molecular iodine for the eradication of pathogens including *S. aureus* and antibiotic resistant microbes from the upper respiratory tract of mammals and for inhibiting the activation of immune cells. Molecular iodine is also employed in the inhibition of superantigens in the treatment of atopic dermatitis, eczema, psoriasis, impetigo or sinusitis.

BACKGROUND OF INVENTION

Nasal carriage of *Staphylococcus aureus* is a well-defined risk factor for subsequent infection in nearly all categories of hospitalized patients that have been studied. *S. aureus* carriage has been studied extensively in surgical patients (general, orthopedic, and thoracic surgery), in patients on hemodialysis, in patients on continuous ambulatory peritoneal dialysis (CAPD), HIV-infected patients, and in patients in intensive care units.

The morbidity and mortality and economic impact of surgical-site infections (SSIs) are enormous. SSIs, the most common nosocomial infections among surgical patients, are thought to complicate approximately 500,000 of the estimated 27 million operations performed annually in the United States. *S. aureus* is the most frequently identified pathogen in SSIs. The estimated annual hospital charges associated with these infections is more than $1.6 billion. SSIs prolong hospital stays by more than 5 days per episode. More importantly, SSI patients are more than twice as likely to die in the postoperative period.

The pathogenicity of *S. aureus* is normally associated with the ability of a particular strain to produce coagulase enzymes but these organisms contain antigens and produce toxins with superantigenic properties and have been implicated in at least two disease states. *S. aureus* enterotoxins activate T-cells by binding to the variable beta-chain of the T-cell receptor major histocompatibility class II complex (MHC) outside of the antigen specific groove. Clinical studies demonstrate that bacterial superantigens induce Ig-E synthesis which may have a major impact on upper and lower airway disease such as nasal polyposis and asthma.

Elimination of *S. aureus* nasal carriage seems to be the most straightforward strategy to prevent the real and potential negative affects of *S. aureus* in the nasal cavity as well as other areas of the upper respiratory tract which for purposes of the present invention is defined to include the nose, paranasal sinuses, pharynx, trachea, bronchi and the mouth. The introduction of mupirocin ointment in the late 1980s was intended to meet this need. Mupirocin nasal ointment is an effective treatment for eliminating *S. aureus*. The treatment of carriers with mupirocin in the nasal cavity results in a significant reduction of the nosocomial *S. aureus* infection rate for hemodialysis and CAPD patients. A review mupirocin studies concluded that treatment of *S. aureus* carriers with mupirocin in the nasal cavity significantly reduces (50%) of the rate of nosocomial *S. aureus* infection. Many randomized and non-randomized mupirocin trials indicate that mupirocin nasal treatment of patients prior to surgery reduces *Staphylococcus aureus* postoperative infection.

Mupirocin resistant strains were described soon after its introduction. Moreover, the increased use of mupirocin, especially for chronic infections, has led to an increased incidence of resistance. In a recent survey from Spain, levels of mupirocin resistance in clinical isolates was reported to have increased for 7.7% in 1998 to 17% in 2000, and some hospitals have reported incidences as high as 63%. The continuing spread of methicillin resistant *S. aureus* (MRSA) and the increase in mupirocin-resistant strains prevents the prophylactic use of this product and highlights the need for alternative agents. Before mupirocin can be administered to a patient suspected of being a *S. aureus* carrier they must be tested for the presence of *S. aureus* in their nasal nares. This requires a medical professional to swab the nasal cavity for subsequent evaluation for the presence of *S. aureus* by a microbiology laboratory; a process that takes at least 24 hours and often 48 hour.

Most investigators studying mupirocin for elimination of *S. aureus* carriage in hospitalized patients have commented that prophylactic use or generalized pre-surgical application will lead to increased rates of mupirocin resistant *S. aureus*. In some cases investigators have looked for alternative treatments to eradicate *S. aureus* from nasal nares. One well-known antimicrobial agent, polyvinylpyrolodone-iodine (PVP-I), has been investigated by several groups for eradicating *S. aureus* and MRSA in the nasal cavity.

In these studies PVP-I was diluted to reduce potential toxicity and the results were promising. These investigators point out that PVP-iodine provides useful properties for local anti-infective treatment in general and for surface decontamination in particular. The microbial action spectrum is broad even after short exposure times and no known microbial resistance to iodine occurs. In contrast to antibiotics PVP-I not only destroys bacteria, but also effectively inhibits the release of pathogenic factors, such as exotoxins, endotoxins and tissue-destroying enzymes.

The label claim on iodine-based germicides is based on "total iodine" which is measured by thiosulfate titration. Unfortunately, three species of iodine are titrated by thiosulfate: triiodide, HOI (hypoiodious acid) and $I_2$. The overwhelming majority of the iodine titrated in these germicides exists as triiodide. The high concentrations of iodide, buffering agents (pH<4) and povidone in these germicides are included to improve the stability of the $I_2$ molecule.

The formulators of these compositions did not give consideration to use in the nasal cavity. The prior art applications using iodine in the nasal cavity make no attempt to optimize the efficacy to toxicity properties of these agents as they are intended for use on the skin. When these agents are applied to the skin the only species of iodine that are of concern with respect to systemic toxicity is the $I_2$ species since it is the only species of iodine that can penetrate the skin. When PVP-I is applied to the skin of mammals less than 0.01% of the iodine contained in these compositions is absorbed systemically. Consequently, the amount of iodine that is absorbed systemically is so low that it is not possible to detect the increase in systemic iodine (if any) above the background level. Consequently, the ratio of $I_2$ to other iodine species in complex iodine formulations applied to the epidermis is not a meaningful safety consideration. However, when iodine-based compositions are applied to mucous membranes the risk to the thyroid is distinct. For instance, when PVP-I is administered to the nasal cavity 100% of the iodine administered is absorbed systemically.

Kramer in *Dermatology* Vol. 204 (Suppl.) 1; 86-91, 2002 examined the irritation potential of iodophors in the nasal cavity and cartilage tissue. The hen's egg-chorioallantoic membrane (HET-CAM) test and explant test was used to evaluate the tolerability of and PVP-I. As shown in the Table below 10% PVP-I inhibits growth.

TABLE

Growth rates in explant test with prepared peritoneal tissue.

| Agent | Concentration | Exposure min | Growth rate % (control = 100%) |
|---|---|---|---|
| PVP-I | 10% | 1 | 63 |
| | 10% | 30 | 40 |

Masano in *Postgrad Med J* 1993, 69 *Suppl* 3, S122-5 treated patients and healthcare workers with PVP-I cream. Daily application of 10% PVP-I for 2 months did not induce goiter but the TSH levels in four of seven family members was elevated. These results indicate that iodine, like almost all other chemical and biological ingredients in nasal formulations, is absorbed in the nasal cavity. Kramer and Gluck in *Krankenhaus-und Praxishygiene* (Hospital and Practice Hygiene); Kramer, A., Heeg, P. et al., Eds.; München, Fischer BEI Elsevier: 2001; pp 252-268 recognized safety concerns related to the use of agents with high levels of iodine and diluted PVP-I to a concentration of 1.25% before application in the nasal cavity. A total of 88 volunteers (77 males and 11 females) were treated twice a day for three days and the principal side effects reported were dryness, itchiness and sneezing. No thyroid dysfunction was observed. The prior art does not describe an approach that provides a composition with a high therapeutic index (ratio of efficacy to side effects).

U.S. Pat. No. 6,171,611 describes a nasal moisturizing saline (0.65%) solution made of water, iodine or an iodine salt that is buffered at physiological pH, namely pH 7.4 but does not identify the basic formulation parameters that would enable one to devise a biocidal composition of matter. The iodine described in U.S. Pat. No. 6,171,611 is either "iodine" or an "iodine salt" selected from the group consisting of ammonium iodate, ammonium iodide, calcium iodate, calcium iodide, iodine monochloride, iodine trichloride, magnesium iodate, magnesium iodide, potassium iodate, potassium iodide, sodium iodate, sodium iodide, zinc iodate and zinc iodide. It is well known to one skilled in the art that these iodide salts are not, biocidal; in fact, at a pH of 7.4 the iodide salts in this group are not biocidal either individually or when combined. Moreover, a pH of 7.4 is not compatible with the $I_2$ species since $I_2$ is not stable at a pH of 7.4 and at a pH of 7.4 the $I_2$ species hydrolyzes very rapidly to form other species of iodine including iodide, HOI, iodate and triiodide. U.S. Pat. No. 5,962,029 describes the hydrolysis of $I_2$ at a pH of 7 and above. At a pH of 7.0 about 21% of the $I_2$ is hydrolyzed in one hour; at a pH of 8.0 the loss increases to 78% in one hour. This is not a new observation since the rate of hydrolysis of $I_2$ was first published over 50 years ago by Wyss in *Arch Biochem* 1945, 6, 261-268.

König et al. in *Dermatology* 1997, 195 *Suppl* 2, 42-48 studied the effect of PVP-I on polymorphonuclear leukocytes (PMN) cells. PMN cells play a role in the immune response by engulfing a foreign pathogen and processing it prior to presenting the processed antigen to the immune system. PMN cells engulf a pathogen using a process known as phygocytosis. Following phagocytosis, the pathogen is moved into a phagolysozome where degredative enzymes actively lyse the pathogen. When pathogens are lysed they release proteins like TNF-α which can stimulate an immune response. Immune responses like these are well known in several medical conditions including atopic dermatitis, eczema, psoriasis, impetigo and sinusitis. König et al. combined a *S. aureus* strain of unknown enterotoxin status with various concentrations of PVP-I, added PMN cells and then incubated the mixture for 6 hours. The data indicate that PMN cells released increasing amounts of TNF-α as PVP-I is diluted demonstrating PVP-I inactivation of the cytokine TNF-α after its release from PMN cells. The PVP-I reaction observed by König was a PMN-specific response (recognition-phagocytosis-processing).

Hill and Casewell *J Hosp Infect* 2000, 45, 198-205 demonstrated that the nasal secretions from 11 different samples reduced the biocidal activity of PVP-I. They calculated that 1.0 milliliter of nasal secretions inactivated the equivalent of approximately 22.5 mg of PVP-I. This is not a surprising result since it is known that the nose has a well defined mucociliary apparatus. Airway mucus consists of two layers, a low vicoelasticity periciliary layer that envelops the cilia, and a more viscous layer that rides on top of the periciliary layer. The primary glycoproteins that comprise nasal mucous are mucins. Mucins contain a very high concentration of cysteine which can react with $I_2$ and thereby neutralize its activity. Consequently, it is necessary to insure a minimum $I_2$ concentration that can overcome whatever residual mucin resides in the nasal cavity.

Given the presence of a bioburden in the nasal cavity, one of the key formulation parameters is the minimum concentration of biocidal iodine (i.e., $I_2$) required for efficacy. In theory, the concentration of $I_2$ is a function of the amount of material that is contacted to the interior of the nasal cavity. In practice, it is only feasible to use about 0.25 grams of material per nostril if the formulation is provided in the form of a gel, cream or ointment and no more than two times that amount (i.e., 0.5 grams per nostril) if the formulation is delivered as a liquid in the form of nose drops or a spray. U.S. Pat. No. 6,171,611 claims a lower concentration range of 0.001% iodine by weight which is equivalent to 10 ppm $I_2$ (assuming that all of the iodine species were present in the biocidal form). It has been found in accordance with the present invention that a concentration of 10 ppm $I_2$ is not adequate to eliminate *S. aureus* when the formulation is provided as a gel. Even when the composition is sprayed into the nasal cavity, thereby allowing a larger number of $I_2$ molecules to contact the mucous membranes of the nasal cavity, a 10 ppm composition is not adequate to overcome the bioburden associated with endogenous mucin.

DEFINITIONS

The term "molecular iodine" as used herein refers to the $I_2$ species which is often referred to as diatomic iodine or elemental iodine in the literature. The term molecular iodine refers to $I_2$ that can react with pathogens in that the $I_2$ is not complexed with other molecules.

The term "iodide anion" as used herein, refers to the species that is represented by the chemical symbol $I^-$. Suitable counter-ions for the iodide anion include sodium, potassium, calcium and the like.

The term "triiodide" as used herein, refers to the species which is represented by the chemical symbol $I_3^-$. It is recognized by one skilled in the art that triiodide can dissociate into one iodide anion and one molecule of free molecular iodine.

The term "total iodine" as used herein, refers to the iodine contained in all of the following iodine species: free molecular iodine, iodide, organically complexed forms of iodine, triiodide, iodate, iodite, hypoiodious acid (HOI) etc.

The term "therapeutic index" has traditionally been defined as the ratio of the desired effect to the undesired effect. It should be noted that a single drug can have many therapeutic indices, one for each of its undesirable effects relative to a desired drug action. $I_2$ is the sole biologically active form of iodine in the anticipated compositions; toxicity is associated with all forms of iodine. Therefore, the term "therapeutic index" as used herein, refers to lowest concentration of total iodine that achieves the desired clinical effect.

The term "unpleasant odor" from $I_2$ refers to the vapor pressure of $I_2$ generated at 20° C. from 0.15 mL of a composition that will, within 67 seconds, turn a moistened 1 inch strip of potassium iodide starch paper (Whatman International, Ltd, Cat No. 2602-500A) blue when said starch paper is vertically aligned with and adhered to the top inside of a sealed 50 mL self-standing graduated plastic tube (Corning Cat No. 430897).

The term "rate of iodine generation" as used herein, refers to the rate at which molecular iodine is formed. The compositions in the present application all need to be activated by mixing and then applied to the surface of interest. Application of the compositions in this application should occur from 20 seconds to 60 minutes after mixing; therefore, the rate of $I_2$ generation is a meaningful consideration.

The term "ratio of molecular iodine" as used herein, refers to the ratio of molecular iodine ($I_2$) to all other iodine species including complexed iodine.

The term "superantigen" refers to a class of immune stimulants that are unique because they do not require cellular processing and presentation to elicit a response. The *S. aureus* enterotoxin B is a potent enterotoxin. Superantigens indiscriminately activate T-cells of the immune system causing localized as well as system-wide inflammatory responses including synthesis and release of cytotoxins. Superantigens are secreted as exotoxins by bacteria Superantigens bind externally to the Vβ domain of the T-cell receptors (TCR) and to the complementary chain of major histocompatibility complex type II molecules (MHC II) causing antigen-independent T-cell activation.

The term "iodination" refers to the chemical addition of an iodine atom to an organic molecule. Iodine is known to iodinate the amino group, sulphydral groups, aromatic carbon atoms containing hydroxyl groups and unsaturated bonds.

SUMMARY OF THE INVENTION

In accordance with the present invention the minimum concentration necessary to provide an effective biocidal activity in the upper respiratory tract is 25 ppm 12. This minimum value is based upon quantitative microbiological measurements with swabs taken from the nasal cavity. Accordingly, when iodide and iodate are used as the reductant and oxidant species a minimum concentration of 20 ppm of iodide and 6.9 ppm iodate is required respectively when the ratio of generated $I_2$ is at least 40%.

A major consideration when formulating $I_2$ for use in the nasal cavity is the vapor pressure of the $I_2$ molecule. Iodine vapor is considered to be more irritating on a molar basis than either chlorine or bromine vapor. Iodine vapor causes nose and throat irritation, coughing, wheezing, laryngitis. The Canadian Center for Occupational Health and Safety indicate that repeated exposure to iodine vapor or exposure to high concentrations of iodine vapor may cause airway spasm, chest tightness, breathing difficulty, severe inflammation and fluid accumulation in the voice box, upper airways and lungs. Humans can work undisturbed at 0.1 ppm of atmospheric $I_2$; with difficulty at 0.15-0.2 ppm and are unable to work at concentrations of 0.3 ppm. However, the odor threshold for $I_2$ has been reported at 0.9 ppm so irritation may occur before the odor is detected. Clearly, if an odor is detected than the level of $I_2$ is not optimal. Given the well established safety concerns for $I_2$ in the vapor phase it is necessary to maintain a level that will not cause harm.

At 25° C. and 1.0 atmosphere of pressure the equilibrium constant for sublimation of $I_2$ is $4 \times 10^{-4}$. This equilibrium accounts for the $I_2$ vapor pressure of 0.3 mm at 25° C. and 1.0 mm at 38.7° C. Using standard atmospheric pressure, a maximum concentration of atmospheric $I_2$ of about 1300 ppm could build up at body temperature. Therefore, administration of $I_2$ in the nasal cavity can lead to an unpleasant odor. If a strong odor is detected with a particular formulation then the nasal mucosa is being exposed to a concentration of $I_2$ that has been established as unsafe. The upper limit of $I_2$ in water is 330 ppm so it is theoretically possible to obtain a concentration of 300 ppm $I_2$ in a totally aqueous formulation which would fall within the scope of this application. It has been found that a 300 ppm $I_2$ solution emits an odor that is easily detectable by humans and is not optimal for repeated administration in the nasal cavity.

The characterization of an odor from $I_2$ is related directly to the vapor pressure of $I_2$ in a particular formulation. Some agents suitable for incorporation in the formulations contemplated in this application e.g., cyclodextrins, have the ability to reduce the vapor pressure of $I_2$ even while the $I_2$ species remains chemical active, i.e. detectable by potentiometric analysis. The actual potential to generate a detectable odor from 12 in a particular formulation must be measured and cannot be predicted for most formulation matrices other than water.

Efficacy, as determined by the elimination of *S. aureus*, must be balanced against 12 odor and nasal irritation when establishing the upper level of $I_2$ suitable for use in a nasal formulation. A 300 ppm concentration of $I_2$ at 37° C. produces a strong odor which is not optimal. It is clear that the optimum use concentration of $I_2$ is the minimum necessary to eliminate *S. aureus* from the nasal cavity. It was found that an appropriately formed gel formulation containing 250 ppm of $I_2$ were acceptable with respect to odor. For the purposes of this application the preferred concentration of $I_2$ is one that yields a vapor pressure that is equal to or less than that observed in a 250 ppm solution of $I_2$ in 0.1 N hydrochloric acid.

The residence time for an agent applied to the nasal cavity is affected by a variety of factors. One of these is the location of deposition since deposition in the anterior portion of the nose provides a longer nasal residence time. A second consideration is the viscosity of the composition as a higher viscosity provides a longer residence time. This application anticipates formulations with a viscosity that ranges from a value that is substantially similar to water (i.e., 1.0 cp) to values with a viscosity of 40,000 cp. The speed of kill from $I_2$ is extremely rapid (seconds) and the residence time is not anticipated to be a significant a factor the inherent bioburden in the nasal cavity or the issue of insuring that $I_2$ is uniformly disturbed within the nasal cavity so it can contact pathogens.

The pH of the nasal mucosa is preferentially maintained in a range of 4.5 to 6.5 since this allows the endogenous lysozyme to inactivate bacteria. In addition, normal ciliary movement is maintained within this pH range. $I_2$ can be formulated to remain stable during the anticipated residence time of the drug in the nasal cavity in this pH range. The preferred pH range of the formulations described in this application lies between 3.0 and 6.0. The volume of a gel medicament per nostril anticipated in this application is between 25 to 500 μL with 100-250 μL being the most common dose volumes. If the formulation has a viscosity that is 10 cp or less then a volume as large as 3 mL may be administered. Therefore, an adequate formulation buffer capacity is required to maintain the desired pH in situ. The use of preservatives to prevent microbial growth is anticipated in this application provided that such preservatives are effective between pH 2.0 and 6.0. Humectants are anticipated in this application and can be added easily in gel-based nasal products; common examples include glycerin, sorbitol and mannitol.

Iodine is a relatively bulky atom with a molecular weight of 129. The interaction between T-cell receptor (TCR) and *Staphylococcus aureus* enterotoxin (SE) superantigen is blocked by the covalent binding of $I_2$ with amino acids within the binding domain. The net effect of these reactions is to prevent the binding reaction between *S. aureus* superantigens and T-cell receptors. This means that $I_2$ can prevent the binding of SE to T-cell receptors in the absence of *S. aureus* since *S. aureus* secretes SE into the medium surroundings the bacteria. Examples of these locations include the nasal vestibule, sinuses, skin and wounds. In addition, $I_2$-binding to these amino acids may block the ability of kinases to add phosphate groups to tyrosine, serine, histidine and threonine which would, in turn, block cell signaling processes. The ability of $I_2$ to interfere with both T-cell binding via superantigen and protein phosphorylation prior to cell signaling provides a previously unidentified means to mitigate the severe immune responses caused by *S. aureus*.

The present invention describes a method to inhibit a lymphocyte/T-cell response that does not have a phagocytic processing step and therefore inhibit a lymphotyte/T-cell response to enterotoxin. In fact the method of the present invention teaches how to block the superantigen binding to the T-cell receptor. This invention also describes a method that will eradicate *S. aureus* from the upper respiratory tract but not irritate the nasal tissue or cause systemic toxicity.

DESCRIPTION

The formation of $I_2$ in an aqueous composition is preferably generated in accordance with this invention from a reaction by an oxidant and a reductant in a manner such that at least 40% of the total iodine present in the aqueous composition is $I_2$ at a minimum concentration of $I_2$ above about 25 ppm. The concentration of $I_2$ contemplated in this application ranges from 25 ppm up to 250 ppm with at least 40%, but preferably at least 50%, of the total iodine being in the form of 12. The preferred concentration of $I_2^-$ is from 25 ppm to 150 ppm. The most preferred concentration of molecular iodine is from 50 ppm to 75 ppm.

The concentration of total iodine contemplated in this application ranges from 25 ppm up to 500 ppm. The preferred concentration of total iodine is from 25 ppm to 300 ppm. The most preferred concentration of total $I_2$ is about 50 to 150 ppm.

The ratio of $I_2$ contemplated in this application ranges from 40 to 100%. The preferred ratio of molecular iodine is from 70 to 100%. The most preferred ratio of molecular iodine is 100%.

The rate of iodine generation is defined herein, as the time required for the generation of $I_2$ to reach a maximum value. The rate of iodine generation contemplated in this application ranges from seconds for diffusion controlled reactions such as that between iodide and iodate in an aqueous environment to a high of 15 minutes. The most preferred rate of $I_2$ generation contemplated in this application is 2-5 seconds. It is possible to practice this application by diluting stable compositions of iodine and then immediately applying the product of said dilution. This approach is also contemplated under the current application and would be considered to have an instantaneous rate of $I_2$ generation.

Numerous methods known in the art can be utilized to generate $I_2$ as contemplated in this application. For in situ generation of $I_2$ from iodide the most common oxidants are active chlorine compounds and hydrogen peroxide. The preferred oxidant to generate $I_2$ from iodide is iodate. Iodate can be introduced as a salt from the following group: calcium iodate, sodium iodate, potassium iodate, magnesium iodate, zinc iodate, ammonium iodate, and the like. Molecular iodine can also be generated by dilution of formulations that contain complexed iodine or by dissolution of elemental iodine as is done in several devices utilized for water disinfection.

Suitable dry sources of iodide anion include sodium iodide, calcium iodide, ammonium iodide, magnesium iodide, zinc iodide and potassium iodide as well as other salts of iodide. Any compound that yields iodide anion upon dissolution in an aqueous environment is suitable for this application. The simple salts of iodide are preferred and have the advantage of being less costly. Additionally, they have a long shelf life in solid and liquid form.

The types of compositions contemplated under this application include liquids, gels, creams, ointments and emulsions with the proviso that oil-based creams and emulsions are not contemplated in this application. The type of composition is not a determinative aspect of this application rather the absolute and relative concentration of $I_2$ and complexed $I_2$ are the two most critical aspects of this invention. Examples of the different types of compositions are provided, by way of example, in the Examples section of this application. It is clear from these experiments that many different types of compositions are compatible with the teachings of this application.

The thickeners useful in the context of the invention are preferably taken from the group consisting of alkyl celluloses, the alkoxy celluloses, xanthan gum, guar gum, polyorgano sulfonic acid and mixtures thereof. The thickeners are chosen based on compatibility with the other formulation ingredients and desired viscosity. Generally speaking the thickener should be present at a level of from about 0.01-10% by weight, and more preferable from about 0.1-1% by weight.

Cyclodextrins are crystalline, water soluble, cyclic, non-reducing, oligosaccharides comprised of glucopyranose units. $I_2$ is substantially less hydrophilic than water, and therefore has the potential to be included in the cyclodextrin cavity in the presence of water. Such complexation of $I_2$ with a cyclodextrins reduces its capacity to evaporate. There are three classes of cyclodextrins (i.e., $\alpha$, $\beta$ and $\gamma$) comprised of 6, 7 and 8 glucopyranose units respectively. Cyclodextrins are potentially useful for the formulations contemplated in this application since they can bind $I_2$ and thereby reduce the effective vapor pressure of $I_2$ in a formulation.

Suitable buffers for the compositions contemplated in this application include water and hydroalcoholic mixtures buffered with glycine, phthalic acid, citric acid, phosphates, dimethylglutaric acid, acetate, succinic acid, phthalic acid, malic acid, boric acid, and the like. The commonly available salts of these agents, e.g. sodium citrate, potassium phosphate, calcium maleate, are equally suitable for use in this compositions contemplated in this application.

Generally, any dispersible conditioning agent, humectants and emollients, known to those of skilled in the art may be used in the present invention. Preferred emollients to be used in the invention are taken from the group consisting of glycerin, propylene glycol, sorbitol, lanolin, lanolin derivatives, polyethylene glycol, aloe vera, glucamate polyethoxylated glucose dioleates containing at least 100 ethoxy units in the polyethylene glycol moiety, available, polyethoxylated methyl glucose containing at least 10 ethoxy units, allantoin, alginates, monoester salts of sulfosuccinates, alphahydroxy fatty acids, esters of fatty acids, ceramides, and mixtures thereof. Broadly, the conditioning agents are used at a level of from about 0.5-20% by weight. The most preferred conditioning agents are sorbitol, mineral oil, glycerin and/or mannitol, and are usually employed at a level of from about 1-20% by weight, and more preferably from about 2-10% by weight.

Chelating agents or sequestrants can be useful stabilizing agents in the invention particularly when a complexed form of iodine is present. Commonly available chelating agents can be used in the invention including both inorganic and organic chelating agents. Organic chelating agents include alkyl diamine polyacetic acid, chelating agents such as EDTA (ethylenediamine tetracetic acid tetrasodium salt), acrylic acid and polyacrylic acid type stabilizing agents, phosphonic acid and phosphonate type chelating agents and others. Preferable organic sequestants include phosphonic acids and phosphonate salts including 1-hydroxy ethylidene-1,1-diphosphonic acid, amino [tri(methylene phosphonic acid)], ethylene diamine [tetra(methylene-phosphonic acid)], 2-phosphonobutane-1,2,4-tricarboxylic acid as well as alkali metal salts, ammonium salts, or alkyl or alkanol amine salts including mono-, di- or triethanol amino salts. Inorganic chelating agents include commonly available polyphosphate materials such as sodium pyrophosphate, sodium or potassium tripolyphosphate along with cyclic or higher polyphosphate species. Preferably, such a sequestering agent is used at a concentration ranging from about 0.05 wt % to about 0.5 wt % of the composition.

Commonly available organic acids that can be used in the invention include benzoic acid, mandelic acid, sorbic acid, citric acid, lower alkanoic acids and their food-grade salts, such as the sodium potassium or ammonium salts thereof. These organic acids, their salts, or mixtures thereof are present in the composition in an amount between about 0.010 to 0.5 percent by weight, preferably from 0.050 to 0.20 percent by weight. The presently preferred organic acids are mandelic acid, benzoic acid, citric acid and sorbic acid, with benzoic acid suitably present as sodium benzoate and sorbic acid suitably present as the free acid. Each of these acids, or their salts, and others, alone or in combinations, can be incorporated into the compositions contemplated in this invention.

The present invention demonstrates that a dose dependent application of molecular iodine reacts with *Staphylococcus aureus* enterotoxin superantigen and renders it incapable of binding to T-cell lymphocytes as measured by the failure of T-cells to synthesize and release various cytokines. The ability of iodine to interfere with T-cell binding of superantigen in a dose-dependent fashion is a novel observation of the present invention.

The teachings and examples in this application do not make any attempt to specifically enumerate the entire prior art in the area of topical iodine preparations. Excipients that are known to be compatible with iodine may also be of use with compositions and conditions described in this application. Such excipients include surfactants, thickeners, humectants, emollients, skin conditioning agents, stabilizing agents, opacifiers, wetting agents, essential oils, chelating agents, buffers, preservatives, organic acids and fragrances.

EXAMPLES

Example 1

Nasal secretions were gathered from 10 volunteers (7 males and 3 female) after exercise in cold air (between 20 and 35° F.); four of the volunteers had colds. Dripping or blown secretions were collected in plastic graduated beakers (Fisher, Scientific) and the tops were covered with Parafilm M. The initial samples were frozen until all samples were collected. Samples were mixed with water (2 part sample to 1 part water (v/v)) and vortexed in a pulsatile manner until all samples were substantially homogeneous and uniform aliquots were able to be removed with a pipette.

Iodine crystals (ACS Reagent Grade, Sigma-Aldrich) were placed in a 1 liter volumetric flask and then 0.01N HCl was added to the flask QS to 1 liter; a rubber stopper was placed in the top of the flask to prevent evaporation. The rubber stopper had a small glass tube inserted through it; the top of this tube was sealed with parafilm. The $I_2$ crystals were stirred at room temperature for 3 hours with a magnetic stir bar and magnetic stir plate. After two hours the glass tube was pushed down such that the bottom of the tube was located at a point about 3 inches above the bottom of the flask. Samples of the saturated $I_2$ solution were withdrawn through this glass tube by using 50 mL glass syringe with an 18 gauge hypodermic needle that had a thin plastic tube (PVC ID 0.046") attached to its end. The stopper was therefore maintained on the flask at all times. Samples of the stock $I_2$ solution were withdrawn and the concentration of $I_2$ was determined to be 330 ppm using the potentiometric method of Gottardi.

A 0.25 mL aliquots of the vortexed nasal secretions were placed in a 1 dram vial (15×45 mm) vial and a cap was placed on the top. Aliquots of a pH 5.0 citric acid buffer (100 mM) was placed in 7 dram vials (29×65 mm) and sealed by placing a thin plastic cap onto the vials. One mL of the stock $I_2$ solution was injected into the vials containing 1, 3, 6, 10 or 15 mL of the 100 mM citric acid buffer; this yielded solutions containing 165, 83, 47, 30 and 21 ppm 12. A sample (0.25 mL) was withdrawn from each $I_2$ solutions and injected through the plastic cap into the samples of vortexed nasal secretions; the combined samples were mixed by vortex. A control sample received 0.25 mL of citric acid buffer without any 12. All samples were allowed to incubate at room temperature for 10 minutes.

After ten minutes 1.0 mL of 0.5% sodium thiosulfate was added to each sample including the control. Trypticase Soya Agar (TSA) plates were inoculated by spreading 0.5 mL of each sample across the surface of the TSA plates. Plates were incubated for 24 hr at 37 degrees Centigrade. The plates were examined for the presence of bacterial colonies after 24 hours of incubation. The nasal cavity is conducive to bacterial replication since the mucopolysaccharides provide a source of nutrients; consequently, all bacteria need to be eliminated for an agent to be effective. Consequently, plates were scored as either positive (the presence of colonies) or negative (the absence of colonies). The results are shown in Table 1 and indicate that nasal secretions affect the ability of $I_2$ to inactivate pathogens. This result is not surprising since the mucopolysaccharides that comprise nasal secretions contain a relatively high percentage of sulphydral groups.

TABLE 1

Effect of Nasal Secretion of $I_2$ Inactivation of Endogenous Nasal Bacteria

| | ppm $I_2$ | | | | | |
|---|---|---|---|---|---|---|
| Sample # | 0 | 21 | 30 | 47 | 83 | 165 |
| 1 | positive | positive | negative | negative | negative | negative |
| 2 | positive | negative | negative | negative | negative | negative |
| 3 | positive | negative | negative | negative | negative | negative |
| 4 | positive | positive | negative | negative | negative | negative |

TABLE 1-continued

Effect of Nasal Secretion of $I_2$ Inactivation of Endogenous Nasal Bacteria

| | ppm $I_2$ | | | | | |
|---|---|---|---|---|---|---|
| Sample # | 0 | 21 | 30 | 47 | 83 | 165 |
| 5 | positive | negative | negative | negative | negative | negative |
| 6 | positive | negative | negative | negative | negative | negative |
| 7 | positive | negative | positive | negative | negative | negative |
| 8 | positive | negative | negative | negative | negative | negative |
| 9 | positive | positive | negative | negative | negative | negative |
| 10 | positive | positive | negative | negative | negative | negative |

Example 2

The minimum concentration of $I_2$ necessary to eliminate S. aureus from the nasal cavity was evaluated in human volunteers. Thirty-five adult volunteers were used to evaluate the ability of different concentrations of $I_2$ to eliminate S. aureus from the nasal cavity. Specimens were taken from the anterior nares of adults by swabing the anterior 1.5 cm of each nasal vestibule with a BBL CultureSwab. The swab was rotated 4 times around the inner walls of each nasal opening and then placed into Stewart's medium and transported to the lab for evaluation. TSA II plates were inoculated with the swabs. The plates were inoculated at 37° C. in a non-$CO_2$ incubator. Following incubation, the TSA II plates were examined for colonies suggestive of S. aureus. S. aureus were identified using standard methods including the Gram stain and coagulase testing. The volunteers were screened for nasal carriage of S. aureus on five separate occasions, 1 week apart. Only persistent carriers (i.e., at least 80% cultures positive) were used for the test.

The test article consisted of a two component get-liquid system. The gel and liquid were mixed prior to application in the nasal cavity with a swab. The gel was prepared using USP citric acid (10% w/v), NF glycerin (10% w/v), NF carboxymethylcellulose (0.75% w/v), NF and boric acid (0.3% w/v); the pH of the gel was adjusted to 3.0 with sodium hydroxide. An aqueous mixture of USP sodium iodide (0.354% w/v) and FCC potassium iodate (0.303%) in sodium carbonate (0.2% w/v) was prepared. The 12 treatment was prepared prior to use by mixing 9 parts of the gel with 1 part of the aqueous solution; this yielded a mixture with 300 ppm $I_2$ as determined by the potentiometric method of Gottardi and by thiosulfate titration.

Seven different concentrations of $I_2$ were used. The different $I_2$ treatments were prepared by mixing different amounts of the carboxymethylcellulose (CMC) gel with the aqueous mixture of iodide/iodate. Table 2 identifies the concentrations of $I_2$ and the relative volumes of gel-iodide/iodate solution used.

TABLE 2

$I_2$ Concentration for Nasal Application

| CMC Gel (mL) | 9.95 | 9.9 | 9.8 | 9.65 | 9.5 | 9.15 | 9 |
|---|---|---|---|---|---|---|---|
| Iodide/Iodate Mixture (mL) | 0.05 | 0.1 | 0.2 | 0.35 | 0.5 | 0.85 | 1 |
| ppm $I_2$ | 15 | 30 | 60 | 105 | 150 | 255 | 300 |

Chronically colonized volunteers were treated with test article for five (4) consecutive days. On each day of treatment the volunteers the activated gel was applied before the start of the work day and then 6 hours later. The CMC gel was mixed with the iodide/iodate mixture and then applied to each of the nostrils of each volunteer with sterile cotton tipped swabs. The CMC gel was activated and then applied within 5 minutes. To apply the gel the swabs were dipped into the activated gel and then rotated inside each nostril; this was done two times for each application with each nostril. Before treatment a BBL CultureSwab was taken to confirm the presence of S. aureus; a second BBL CultureSwabs was taken 24 hours after treatment had ended. Volunteers were also evaluated 1 and 2 weeks after the last treatment.

| | Number of Plates Positive for S. aureus | | | | | | |
|---|---|---|---|---|---|---|---|
| ppm $I_2$ | 15 | 30 | 60 | 105 | 150 | 255 | 300 |
| Pre treatment | 5/5 | 5/5 | 5/5 | 5/5 | 5/5 | 5/5 | 5/5 |
| After Treatment | 4/5 | 0/5 | 0/5 | 0/5 | 0/5 | 0/5 | 0/5 |
| 1 week | 5/5 | 2/5 | 1/5 | 0/5 | 1/5 | 0/5 | 0/5 |
| 2 weeks | 5/5 | 3/5 | 4/5 | 2/5 | 3/5 | 1/5 | 2/5 |

Example 3

A gel of cross-linked acrylic acid was used to evaluate the yield of $I_2$ versus several formulation variables. Cross-linked acrylic acid polymers have rheological properties that may render them useful for use in the nasal cavity. In addition, cross-linked acrylic acid polymers are odor free and have a high number of carboxylic acids groups on the polymer, which helps to maintain a stable acidic pH. Three different gels (B182, NoE-026, NoE-004) were prepared to explore the yield of $I_2$ versus different concentrations of the excipients in the formulation.

| Materials | B182 | NoE-026 | NoE-004 |
|---|---|---|---|
| Carbopol 980 (g) | 5.0 (1%) | 4 (0.8%) | 6.0 (1%) |
| Glycerin (g) | 51 (10%) | 50 (10%) | 60 (10%) |
| EDTA (g) | 0.5 (0.1%) | 0.5 (0.1%) | 0.6 (0.1%) |
| Boric acid (g) | 0 | 0.5 (0.1%) | 0.6 (0.1%) |
| 10 NNaOH (ml) | 5.5 (0.11%) | 17 (1.4%) | 12 (2%) |
| Water (ml) | 440 (88%) | 437 (87%) | 505 (87%) |

A beaker was charged with about 400 ml of water; the polyacrylic acid polymer of interest, e.g. Carbopol 980 NF, was then added and stirred on a Lightnin LabMaster mixer at 800-1000 rpm for 1-2 hour until the Carbopol was hydrated and then the glycerin was added. A solution containing EDTA, boric acid, and 10 N NaOH in 80 ml of water was then added to the mixture. The mixture was then stirred for 1 hour at 600 ppm and stored at room temperature and then QS to 1 liter. A stock solution of sodium iodide and sodium iodate was prepared for admixture with the gel in order to generate defined amounts of 12. Sodium iodide (0.60 grams) and sodium iodate (2.0 grams) was dissolved in 120 ml of water that contained 1.4 ml of 10 N NaOH. The final pH of the gels was between 4.5 and 6.0.

One ml of gel was mixed with 1.0 ml of the stock iodide/iodate mixture. The reactions were stopped at 0.5, 1.0, 2.0, and 4.0 minutes. The gels were then extracted with 10 ml of chloroform and 50 ml of a 1.0 N phosphate buffer pH 4.8 that contains 300 grams of sodium sulfate per liter. The absorbance at 520 nm was measured in a Schimadzu UV-1602 spectrophotometer. Gel NoE-026 was tested prepared freshly and compared to NoE-026 gel stored at 40° C. for 4 months. The yield of $I_2$ was above 50% in all instances; storage of the gels did not appear to impact the yield of 12. The rate of the reaction between iodide and iodate is known to be diffusion controlled and it is not surprising that the yield of $I_2$ was not a function of time.

| | Time (min) | | | |
|---|---|---|---|---|
| | 0.5 | 1 | 2 | 4 |
| | Yield (%) | | | |
| B182 | 63.7 | 66.9 | 66.0 | 69.4 |
| NOE-004 | 64.3 | 65.0 | 58.6 | 59.3 |
| NoE-026 (room temp.) | 65.5 | 73.5 | 67.1 | 63.9 |
| NoE-026 (4 months at 40° C.) | 65.0 | 65.5 | 64.0 | 60.5 |

Example 4

The perceived $I_2$ odor of the formulations contemplated in this application bear directly on utility. The actual potential to generate a detectable odor from $I_2$ in a particular formulation must be measured and cannot be predicted for most formulation matrices other than water. This experiment provides a quantitative means of characterizing the perceived odor from the complex compositions contemplated in this application based upon the $I_2$ odor perceived by humans in an aqueous medium.

Several different concentrations of pure $I_2$ in 0.1N HCl were prepared by dissolution of $I_2$ crystals (Sigma-Aldrich Cat No.266426-250G) in a glass volumetric flask with stopper in place. A 1 inch strip of potassium iodide starch paper (Whatman International, Ltd, Cat No. 2602-500A) was completely moistened with distilled water and vertically aligned flush to the surface of the inside of a 50 mL self-standing graduated plastic tube (Corning Cat No. 430897). Once the start paper was adhered to the inner side of the wall 150 µl of the $I_2$ solutions were transferred into the bottom of the plastic tube; the bottom section of these tubes are conical in shape and hold this volume of fluid in a relatively well defined area. Once the samples were transferred into the graduated plastic tube the top was immediately screwed on and a stopwatch was started. The time required for the starch paper to turn blue was recorded in seconds.

| Starch Paper Coloration from $I_2$ Vapor | | | | | | | | | |
|---|---|---|---|---|---|---|---|---|---|
| | $I_2$ Conc. (ppm) | | | | | | | | |
| | 12.25 | 22.5 | 55 | 110 | 165 | 220 | 250 | 275 | 330 |
| Average Time (sec) | >120 | >120 | 114 | 80.2 | 75.6 | 70.3 | 67.8 | 62.1 | 60.9 |

Five volunteers (3 male; 2 female) were used to evaluate the odor from the aqueous solutions of $I_2$. An odor free room not adjacent to a laboratory, cafeteria or bathroom was used for the evaluation. The individuals selected to evaluate the iodine odor did not have colds or allergies. Tests were conducted in the morning and volunteers were instructed to shower on the morning of the test and not to use lotions or after shave on that morning. The volunteers were instructed to identify any sample that provided an unpleasant odor. None of the volunteers detected any odor at $I_2$ concentrations of 22.5 ppm or less. All of the volunteers were able to detect the presence of a aroma above 55 ppm but this odor was not deemed to be objectionable (4 out of 5 volunteers) until the concentration of $I_2$ was 275 ppm and above.

Example 5

This experiment demonstrates that a dose dependent application of $I_2$ reacts with superantigens, such as *Staphylococcus aureus* enterotoxin B (SEB), rendering them incapable of binding to T-cell lymphocytes. Stimulation of T-cells by superantigen binding is required for cytokine synthesis. The inventors were investigating methods of disinfecting cultured mammalian cells to kill bacteria or fungi/yeast without killing the mammalian cells. The mammalian cells chosen were human peripheral blood leukocytes (PBL) collected fresh using BD vacutainer CPT cell preparation tubes with sodium citrate. Previously described procedures were used to yield highly enriched lymphocytes, which include both B- and T-cells. *Staphylococcus aureus* was obtained from a local hospital on an agar slant. The *S. aureus* isolate was from a patient suffering from food poisoning. The *S. aureus* isolate expressed SEB.

Lymphocytes ($10^6$/mL counted by hemocytometer) were suspended in Hanks' balanced salt solution with HEPES (3 mM) and 2% (v/v) fetal bovine serum and varying amounts of *S aureus* were added ranging from $10^3$-$10^5$ cfu/mL and assays were incubated at 37° C. for one hour. After one hour 500 microliters of $I_2$ was added to various cultures in various concentrations (0.1-100 ppm free molecular iodine, final concentration). After an additional 10 minutes 200 microliters of a 2N solution of sodium thiosulfate was added; 100 microliter aliquots were removed from each reaction vessel and streaked for isolation of *S. aureus* on nutrient agar plates; reaction tubes were then returned to the incubator (37° C.). The results were somewhat predictable. Lymphocyte-*S. aureus* ($10^3$-$10^5$) cultures treated with 0.1-10 ppm of the iodine had viable *S. aureus* that grew on the agar.

Reaction vessels with 10-100 ppm $I_2$ had no viable *S. aureus*. However, the surprising discovery occurred three days later. Each reaction vessel was examined using the microscope/hemocytometer to observe and count the number of lymphocytes. Reaction vessels with $10^5$ *S. aureus* and 10-ppm iodine had 100-fold more lymphocytes (~$10^8$/mL) than similar cultures treated with 100 ppm $I_2$. These results were confusing. We knew that the *S. aureus* strain used in these experiments expressed SEB, a known superantigen. We predicted that something triggered the lymphocyte proliferation at 10 ppm $I_2$ but not at 100 ppm $I_2$ and assumed that it was *S. aureus* SEB. The key assumption was that $I_2$ blocked lymphocyte proliferation at higher $I_2$ concentrations because somehow the $I_2$ blocked a reaction between *S. aureus* and lymphocytes. These results prompted us to perform experiments that might explain the proliferation result.

We decided that the most direct way to test our hypothesis was to mix *S. aureus* SEB with $I_2$; neutralize the mixture with sodium thiosulfate and then treat fresh lymphocytes with the neutralized solution. We could then measure cytokine synthesis following interaction with T-cells. We chose to measure interleukin 6 (IL-6) and interferon gamma (IFN-γ) as markers of T-cell stimulation based on published studies. All reagents including *S. aureus* SEB (US Biological, Swampscott, Mass.; cat# S7965-35A), purified mouse anti-enterotoxin B monoclonal IgG antibody, purified mouse monoclonal IgG to interferon IFN-γ and the cytokine IL-6 were purchased from commercial sources. The control experiments were conducted using fresh PBL and 1 pg/mL SEB. Two site capture ELISA immunoassays in 96 well microtiter plates were purchased as commercial kits IFN-γ (eBioscience, San Diego, Calif.; cat# 88-7314-76) and IL-6 (eBioscience, San Diego, Calif.; cat# 88-7066). The enzyme used was horseradish peroxidase (HRP) and the linkers were biotin-streptavidin, substrate was tetramethylbenzidine (TMB); color development was terminated with sulfuric acid and color was read at 570 nm with a Schimadzu UV-1602 spectrophotometer. The optical density of each unknown was determined and compared to the concentrations of IL-6 and IFN-γ obtained using standards supplied with each commercial kit.

Standard curves were prepared for both IL-6 (6-200 pg/mL) and IFN-γ (0.1-3.0 ng/mL). $I_2$ was prepared fresh at a stock concentration of 330 ppm/mL and aliquots were added to various reaction tubes to achieve the desired final iodine concentration. SEB (10 microliters) was mixed undiluted with $I_2$ (10 microliters) and buffer (IM citrate buffer pH 5.0) at room temperature for 30 minutes. After 1 hour, 5 μL of 2N sodium thiosulfate was added to all samples and gently agitated to insure complete neutralization of the $I_2$. PBL cells, the iodinated SEB were gently mixed in reaction tubes and placed at 37° C. After 1 hour, cells were pelleted and 5 μL was removed from the supernatant of each tube and analyzed for the presence of cytokines IL-6 and IF-γ in the cell-free fraction. Samples of the supernatant were also collected at 12, 24, 36 and 48 hours and analyzed for IL-6 and IFN-γ. The sample wells of the ELISA immunoassays 96 well microtiter plates were washed two times after binding of label to insure removal of all of the sodium azide used to preserve SEB. The results of these assays (shown below) demonstrate that at a concentration of >25 ppm $I_2$ inhibits the ability of superantigens to activate T-cells synthesis of cytokines.

Concentration of IL-6 (pg/ml) versus time

| | Hours | | | | |
|---|---|---|---|---|---|
| $I_2$ (ppm) | 0 | 12 | 24 | 36 | 48 |
| 0 | <6 | 14 | 65 | 104 | 125 |
| 0.1 | <6 | 16 | 71 | 111 | 134 |
| 2 | <6 | 19 | 68 | 89 | 121 |
| 10.3 | <6 | 18 | 74 | 96 | 129 |
| 14 | <6 | 20 | 69 | 99 | 131 |
| 27.5 | <6 | 21 | 72 | 100 | 136 |
| 55 | <6 | <6 | <6 | <6 | <6 |
| 110 | <6 | <6 | <6 | <6 | <6 |

Concentration of IF-γ (ng/mL) versus time

| | Hours | | | | |
|---|---|---|---|---|---|
| $I_2$ (ppm) | 0 | 12 | 24 | 36 | 48 |
| 0 | <0.1 | 0.3 | 0.91 | 1.7 | 2.3 |
| 0.1 | <0.1 | 0.35 | 0.96 | 1.65 | 2.4 |
| 2 | <0.1 | 0.34 | 0.9 | 1.59 | 2.25 |
| 10.3 | <0.1 | 0.32 | 0.89 | 1.68 | 2.44 |

-continued

Concentration of IF-γ (ng/mL) versus time

| | Hours | | | | |
|---|---|---|---|---|---|
| $I_2$ (ppm) | 0 | 12 | 24 | 36 | 48 |
| 14 | <0.1 | 0.29 | 0.96 | 1.66 | 2.35 |
| 27.5 | <0.1 | 0.31 | 0.90 | 1.69 | 2.53 |
| 55 | <0.1 | <0.1 | <0.1 | <0.1 | <0.1 |
| 110 | <0.1 | <0.1 | <0.1 | <0.1 | <0.1 |

We claim:

1. A method for killing or essentially eradicating pathogens including *Staphylococcus aureus* and super antigens resident in the upper respiratory tract of a mammal, said method comprising formulating an aqueous composition containing a source of iodide and iodate at a pH of less than about 6.5 for generating a concentration of between about 25 ppm to about 250 ppm of molecular iodine ($I_2$) in situ through an oxidation-reduction reaction with the source of iodide and iodate being at a minimum concentration of at least 20 ppm of iodide and 6.9 ppm of iodate, respectively and with said molecular iodine ($I_2$) comprising at least 50% of the total iodine atoms in said aqueous composition, and with said aqueous composition having a maximum concentration of $I_2$ which yields a vapor pressure equal to or less than that observed in a 250 ppm solution of $I_2$ in 0.1 N hydrochloric acid at room temperature and administering said aqueous composition to said mammal within a short time period following formation of said aqueous composition containing both the source of iodide and iodate at said minimum concentration levels.

2. The method according to claim 1, wherein said aqueous composition is administered within 20 seconds from the formation of said aqueous composition containing said source of iodide and iodate.

3. The method according to claim 1, wherein the aqueous composition further comprises a cyclodextrin selected from the group consisting of α-cyclodextrin, β-cyclodextrin and γ-cyclodextrin.

4. The method according to claim 1, wherein the range of concentrations of generated $I_2$ is from 50 to 250 ppm.

5. The method according to claim 1, wherein the maximum concentration of $I_2$ is established at or below the detection of an unpleasant odor from $I_2$ by placing the aqueous composition at the bottom of a sealed self-standing graduated plastic cylinder, adhering a moistened 1 inch strip of a potassium iodide starch paper to an upper inner side wall of the plastic cylinder, and allowing time of least 67 seconds to turn the potassium iodide starch paper completely blue at room temperature.

6. The method according to claim 1, wherein the pH of said aqueous composition is in a range from 3.0 to 6.0.

7. The method according to claim 6, wherein said aqueous composition is in a volume from 100 to 2000 μl.

8. The method according to claim 7, wherein said aqueous composition is in a form selected from the group consisting of a liquid, gel, cream, ointment and an emulsion.

9. The method according to claim 8, wherein the aqueous composition is a gel-liquid system.

* * * * *